(12) United States Patent
Stern

(10) Patent No.: US 7,823,598 B2
(45) Date of Patent: Nov. 2, 2010

(54) PORTABLE APPARATUS FOR CHARGING AND CLEANING HEARING AID DEVICE

(76) Inventor: Ari K. Stern, 8126 Township Dr., Owings Mills, MD (US) 21117

( * ) Notice: Subject to any disclaimer, the term of this patent is extended or adjusted under 35 U.S.C. 154(b) by 361 days.

(21) Appl. No.: 11/973,143

(22) Filed: Oct. 5, 2007

(65) Prior Publication Data

US 2008/0128007 A1    Jun. 5, 2008

Related U.S. Application Data

(60) Provisional application No. 60/849,668, filed on Oct. 5, 2006.

(51) Int. Cl.
*B08B 3/00* (2006.01)

(52) U.S. Cl. .................................................... 134/116
(58) Field of Classification Search .................. 134/116
See application file for complete search history.

(56) References Cited

U.S. PATENT DOCUMENTS

| 5,610,494 | A | * | 3/1997 | Grosfilley | .................... 320/113 |
| 2006/0048313 | A1 | * | 3/2006 | Yamaki | ....................... 15/21.1 |

* cited by examiner

*Primary Examiner*—Michael Cleveland
*Assistant Examiner*—Samuel A Waldbaum
(74) *Attorney, Agent, or Firm*—The Weintraub Group, P.L.C.

(57) ABSTRACT

A single portable apparatus for cleaning and charging hearing aids combines the functions of charging and cleaning hearing aid devices into a single unit.

6 Claims, 3 Drawing Sheets

PORTABLE APPARATUS FOR CHARGING AND CLEANING HEARING AID DEVICE

CROSS-REFERENCE TO RELATED APPLICATIONS

This application claims the benefit of U.S. Provisional Application No. 60/849,668, filed Oct. 5, 2006, the disclosure of which is incorporated herein in its entirety.

BACKGROUND OF THE INVENTION

1. Field of the Invention

The present invention pertains to hearing aids and devices for cleaning and charging hearing aids. Even more particularly, the present invention pertains to a single portable apparatus that combines the functions of charging and cleaning hearing aid devices into a single unit.

2. Description of the Prior Art

As is known to those skilled in the art to which the present invention pertains, hearing aids have become miniaturized to the point where they are non-visible or of such miniaturized size that they fit directly into the ear canal. Although this is the most current state-of-the-art there still exists prior art hearing aid devices as well, which envelop the exterior of the ear and are mounted therearound.

In any event, regardless of the type of hearing aid that is involved, these devices present the user with ongoing problems. These devices are very small and use batteries that need frequent charging, and because of their size, small batteries are hard and/or difficult for some users to change. The hearing aid oftentimes does not receive the hygienic care it requires and functionally degrades due to cerumen build-up. There are many reasons for a lack of proper attention, including size of the product, age of the user, or lack of simple and effective way of cleaning. However, there exists an ongoing need to periodically clean the hearing aid, and the battery contained therewithin needs to be recharged.

The prior art has addressed the need for cleaning to a relative degree. By way of example, U.S. Pat. No. 5,649,556 teaches a cleaning device for cleaning an electric razor, which teaches the immersion of the shaving head into a bath of cleaning fluid.

Similarly, U.S. Pat. No. 6,189,215 teaches a device for determining the soiling of the shaving heads. As a consequence of detection of the soil the bath is activated.

It is to be appreciated that the prior art of which applicant is aware simply does not address the issue of cleaning and recharging of hearing aids. Thus it is to be appreciated that there exists a need for such a device. As disclosed hereinafter the present invention addresses this need for improvement.

An object of this invention is the provision of a combined portable apparatus for cleaning and/or charging the battery of a hearing aid device.

In one aspect of this object, the provision of such apparatus that enables a user with the ability to effectively clean and disinfect a hearing aid, including removing cerumen to maintain optimal hearing response of the hearing aid, and maintain proper hygiene.

In another aspect of this object, the provision of such apparatus increases the ease of use and proper functioning of the hearing aid, including reducing/eliminating the need to change batteries and/or dead battery and associated hearing loss.

Another object of this invention is the provision of a combined portable cleaning and charging system for hearing aids that enables a user to place their hearing aids in a base station that acts as a storage, cleaning and recharging station.

SUMMARY OF THE INVENTION

Briefly, a first embodiment according to this invention provides an apparatus for cleaning and recharging at least one hearing aid of the type having an electrical contact on the outer periphery thereof and a rechargeable battery in the interior, comprising:

a base member, said base member including first and second chambers, a receptacle having a cavity for stowing the hearing aid, said receptacle removably mountable in said first chamber and said cavity having a cavity wall in gripping fitment, at least in part, with the outer periphery and the electrical contact of said hearing aid, a reservoir for storing a supply of cleaning fluid, said reservoir provided in said second chamber, electrical circuitry for connecting the electrical contact of said hearing aid, said receptacle, said cavity wall, and the reservoir for storing fluid in electrical circuit relation; and means for connecting the electrical circuitry with a source of electricity.

According to this embodiment of the invention, the fluid reservoir is either formed by the second chamber, and integral with the base member, or provided in a cartridge, removably mounted into the second chamber.

The apparatus includes a switch to selectively place the apparatus in on off mode, a cleaning only mode, and a battery recharge only mode, and indicators in the form of meters and actuatable lights provide visual output indicating the condition of the cleaning fluid, such as viability and pH, the battery charge level, and the time and number of times operated.

According to an aspect of this embodiment of the invention, at least two hearing aids may be cleaned and/or have their batteries recharged.

A second embodiment according to this invention is directed to apparatus for simultaneously cleaning the ear plug and recharging the battery of a hearing aid, the hearing aid including an electrical contact on the outer periphery thereof and a rechargeable battery in the interior in electrical circuit relation with the contact, comprising:

a base station including a top surface and a side wall, a first chamber extending from the top surface into the base and terminating in an interior base wall, and a second chamber extending from the side wall into the into the base, a receptacle for mounting the hearing aid, the receptacle removably mounted in the first chamber and having top and bottom surfaces, and a bore for mounting the hearing aid extending between the surfaces, said bore having a wall, at least in part, engaging the outer periphery of the hearing aid, said chamber having an interior wall, at least in part, engaging the outer periphery of said receptacle and positioning the bottom surface in spaced relation from the bottom wall of said second chamber to form a first reservoir, and said hearing aid ear plug being proximate to the bottom wall when the receptacle is mounted in the first chamber, a fluid cartridge removably mounted in said second chamber, said cartridge forming a second reservoir, a pump, said pump including means for communicating fluid from said second reservoir to said first reservoir, means for communicating fluid from said first reservoir to said second reservoir, electrical circuitry for connecting the electrical contact of said hearing aid, said receptacle, the wall of said bore, the reservoir for storing fluid, and the pump in electrical circuit relation with one another; and means for connecting the electrical circuitry with a source of electricity.

The apparatus, as above described, includes a switch to selectively place the apparatus in on off mode, or in an actuated mode, wherein the apparatus simultaneously cleans the ear plug and recharges the battery of the hearing aid. Additionally, indicators in the form of meters and actuatable lights provide visual output indicating the condition of the cleaning fluid, such as viability and pH, the battery charge level, and the time and number of times operated.

According to an aspect of this embodiment of the invention, at least two hearing aids may be cleaned and/or have their batteries recharged.

The present invention will be more clearly understood with reference to the accompanying Drawings and to the following Detailed Description, in which like reference numerals refer to like parts and wherein:

DETAILED DESCRIPTION OF THE PREFERRED EMBODIMENTS

Turning now to the drawings, FIGS. 1-5 illustrate a portable apparatus adapted to perform the functions of recharging the battery of and/or cleaning a hearing aid. In the discussion that follows, each apparatus shown is adapted to recharge the batteries of or clean hearing aids, whether in a selected sequence or substantially simultaneously. While the apparatuses are shown operating on two hearing aids, an apparatus may be configured to clean and/or recharge only a single hearing aid, or simultaneously clean and/or recharge more than two hearing aids.

Figure 1:
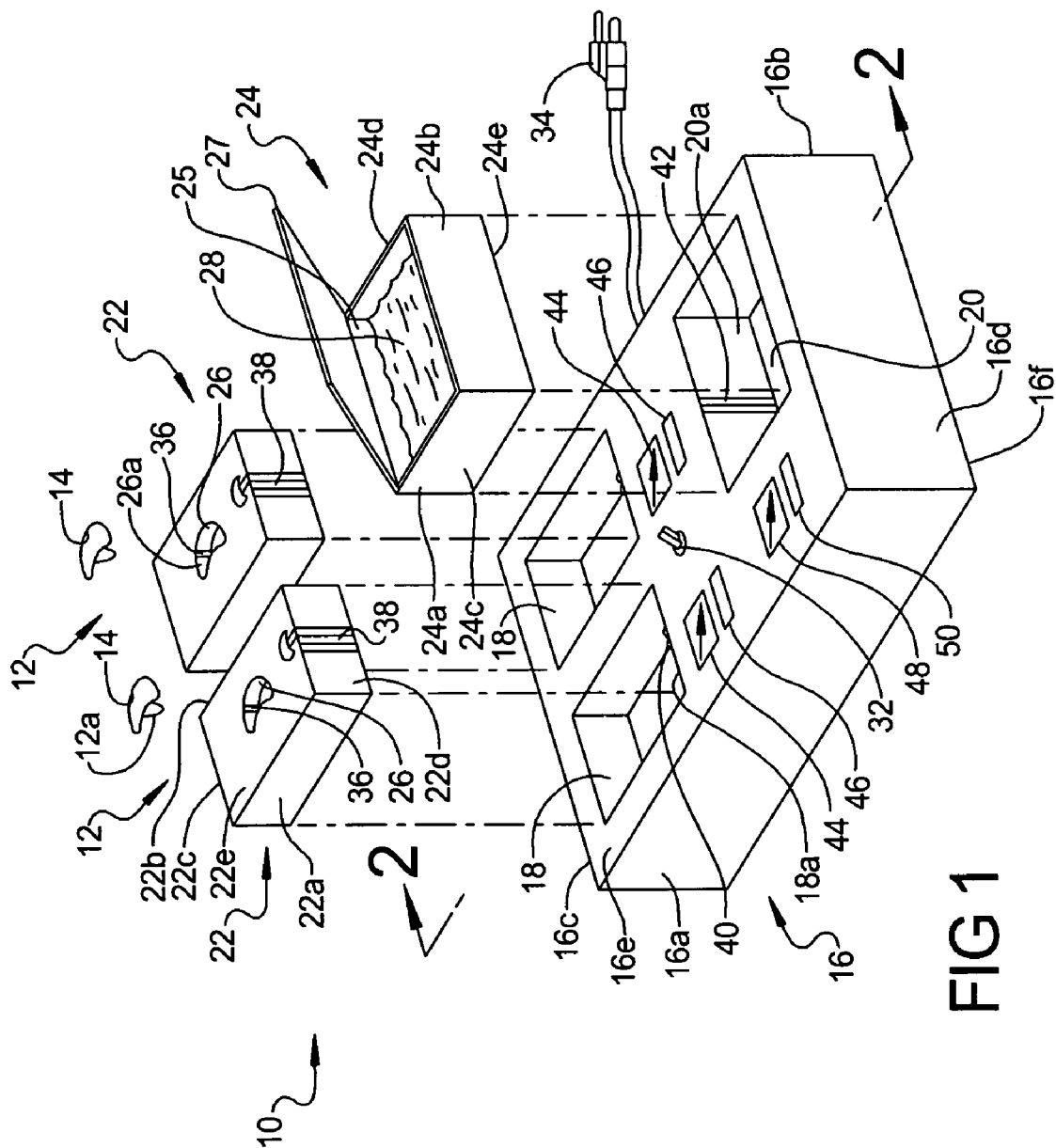
FIG. 1 is a perspective view of a combined cleaning and battery recharging device for a hearing aid according to the present invention, wherein a base member thereof removably receives a receptacle and a cartridge, the receptacle removably mounts the hearing aid, and the cartridge has a reservoir filled with a supply of cleaning fluid.
Figure 2:
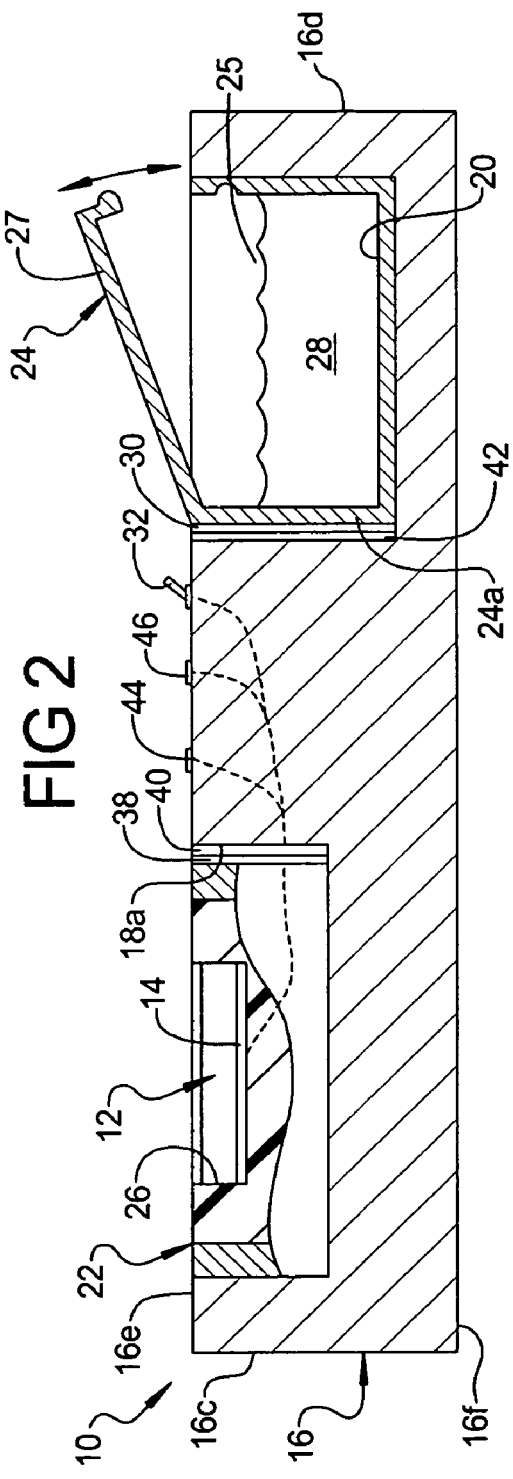
FIG. 2 is a side elevation section view taken along line 2-2 of the hearing aid cleaning and battery recharging device shown in FIG. 1.

Referring to FIGS. 1 and 2, an apparatus for recharging and/or cleaning hearing aids is generally indicated by the reference number 10. The apparatus 10 is adapted to be used with conventionally available hearing aids, generally indicated by the reference number 12. In general, the hearing aid 12 has an outer periphery 12a, generally in the shape of a peanut, and has an electrical contact or contact area 14 on the outer periphery 12a thereof. While not shown, a battery is removably housed within the interior of the hearing aid and disposed in electrical circuit relation with the contact area 14. The battery must be recharged and or replaced from time to time.

The apparatus 10 includes a substantially rectangular shaped base member or station 16 having a pair of opposed side walls 16a and 16b, a pair of opposed end walls 16c and 16d, a top surface or wall 16e, and a bottom surface or wall 16f. It should be noted that the shape of the base station 16 is not limited to a rectangular and/or rectilinear member but may be of any desired geometric configuration, for example, circular and disc shaped.

The base member 16 is provided with a pair of first chambers 18 disposed in side by side relation and a second chamber 20, the chambers 18 and 20 being generally rectangular in shape and extending downwardly from the top surface 16e and into the body of the member 16. The first chamber 18 includes an interior wall 18a and is adapted to removably receive a receptacle 22 associated therewith. The second chamber 20 includes an interior wall 20a and is adapted to removably receive a cleaning fluid cartridge 24 associated therewith.

Each receptacle 22 is generally rectangular and includes outer walls 22a-22d, and a top surface 22e, the outer walls and shape conforming to the rectangular shape of the chamber 18 wherein to enable the receptacle to be snugly fitted within the chamber. A cavity 26, adapted to removably stow a hearing aid 12, extends downwardly from the top surface 22e. As shown, the cavity 26 is formed by an interior wall 26a that conforms to the shape of the outer periphery 12a of the hearing aid, wherein the hearing aid 12 will fit snugly within the associated cavity 26. The cavity 26 may be of any desired shape to conform to the exterior shape of a conventional hearing aid.

The cartridge 24 is generally rectangular and includes outer walls 24a-24d, a bottom wall 24e, which cooperate to form an interior reservoir 25 to receive a cleaning fluid 28, and a lid 27 adapted to sealingly close about the reservoir. The outer wall 24a is provided with an electrical contact pin or contact area 30, wherein to deliver electrical charge to the cleaning fluid 28 in the reservoir, as described in greater detail herein below.

Preferably and according to this invention, the cleaning fluid or solution 28 is one that is compatible for ultrasound or other electrolytic cleaning. Further, the cleaning fluid 28 is organic-based to prevent corrosion of the contact area 14 of the hearing aid 12.

Further, electrical circuitry (not shown), including a switch 32, is provided to selectively turn the apparatus 10 off or connect the apparatus 10 to an electrical source exterior thereto (not shown), either for recharging or cleaning. The exterior electrical service may be provided by an AC source or a battery pack and the connection thereto may be via a conventional electrical plug 34 in electrical circuit relation with the internal electrical circuitry of the apparatus 10.

The switch 32 operates to provide electricity, either to the contact area(s) 14 of the hearing aid(s) 12 for recharging the battery thereof when the hearing aid(s) 12 is in a respective cavity 26, or to the contact 30 of the cartridge 24 for energizing the fluid 28 thereof and cleaning the hearing aid(s) 12 when the hearing aid is immersed in the fluid 28 of the cartridge.

For recharging, the hearing aid(s) 12 is in the cavity 26, and the switch 32 is positioned to complete an electrical path between the electrical contact 14, electrical contact area(s) 36 and 38, respectively, on the interior wall 26a of the of the cavity 26 and the outer wall 22d of the receptacle 22, an electrical contact area 40 on the interior wall 18a of the chamber 18, and the electrical plug 34.

For cleaning, the hearing aid(s) 12 are in the cartridge 24 and immersed in the cleaning fluid 28, and the switch 32 is positioned to complete an electrical path between the electrical contact area(s) 30 on the outer wall 24a of the cartridge 24, and electrical contact area 42 on the interior wall 20a of the chamber 20, and the electrical plug 34

Also, suitable status or condition indicating meters are provided. In this regard, the apparatus 10 includes means for indicating that the battery contained within the hearing aid is fully charged. Although shown as a meter 44 and a charge light 46, separate from one another, other suitable charge indicators may be used.

Additionally, the apparatus includes a meter 48 and light 50, separate from one another, for indicating the pH of the cleaning fluid 28. Additionally, the viability or electrolytic charge of the fluid may be indicated by an appropriate meter. Desirably, visual indication of the status of the cleaning fluid warns the user that the fluid is low and the cartridge needs refilling and/or that the fluid is dirty and needs replacement and/or that that the hearing aid has been appropriately cleaned. Replacement indication may be based on several factors, such as the number of cleaning cycles that have been performed, solution level, or condition of the fluid.

Further, the lights 46 and 50 may be connected to the electrical circuitry in a manner to blink or otherwise provide a visual indication the charging and/or cleaning cycle or operation is complete.

In use, the hearing aid(s) are disposed in a basket or similar device (not shown) to form a unit that is lowered into the reservoir 25 and immersed into the fluid 28. The cartridge 24 is fit snugly into the chamber with the contact areas engaged with one another and the switch turned on, providing electrical current from the plug, thereby energizing the fluid.

The action of electrical potential on a cleaning fluid is described in the above referenced U.S. Pat. No. 5,649,556, the entire contents of which are specifically incorporated herein by reference. Similarly, apparatus for detecting soiling and activating of a fluid bed is described in the above referenced U.S. Pat. No. 6,189,215, the entire contents of which are incorporated herein by reference.

Figure 3:
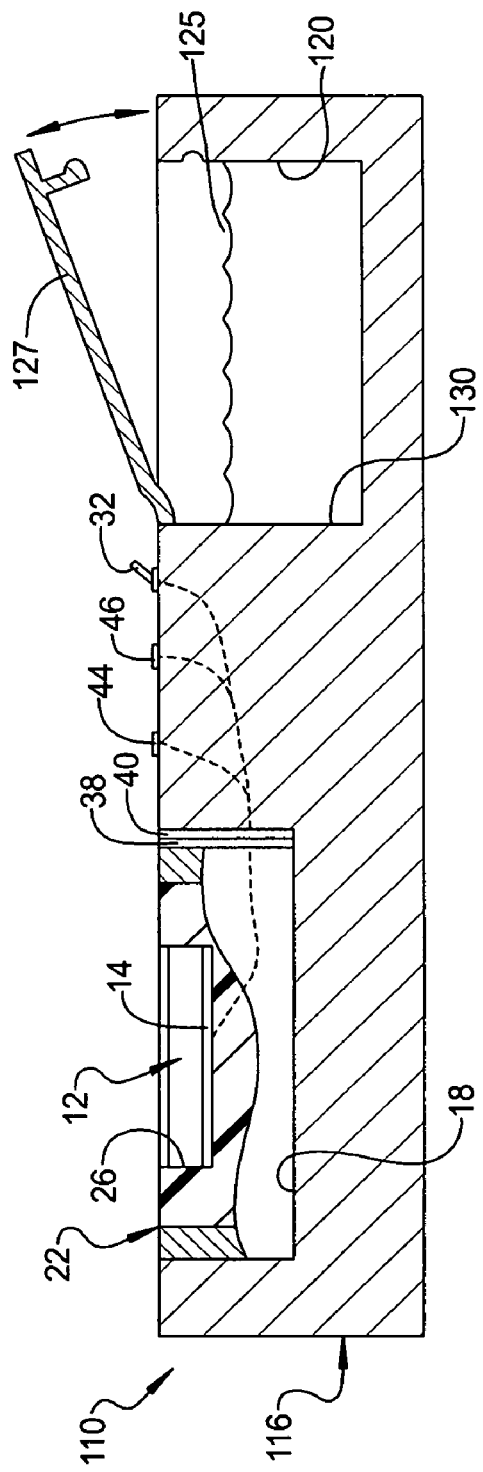
FIG. 3 is a side elevation view of an alternate embodiment of a hearing aid cleaning and battery recharging device, similar to that shown in FIGS. 1 and 2, but wherein a chamber of the base member forms the reservoir that is filled with a supply of cleaning fluid.

Turning now to FIG. 3, an alternate embodiment of an apparatus for recharging and cleaning hearing aids is generally indicated by the reference number 110. In this embodiment, the apparatus 110 is similar to the apparatus 10 described herein above and includes a base member or station 116 that is provided with a pair of first chambers 18, each adapted to receive a respective receptacle 22, a second chamber 120, and the electrical circuitry that is connectable to an exterior source of electricity. The second chamber 120 defines a reservoir 125 adapted to receive the cleaning fluid 28 and a lid 127 is hingedly connected to the top surface of the base member for closing relation about the chamber 120. An electrical pin or contact area 130 is disposed on an interior wall 120a of the chamber 120, the contact area 130 in electrical circuit relation with the electrical circuitry. The indicators and operation are as described herein above.

Figure 4:
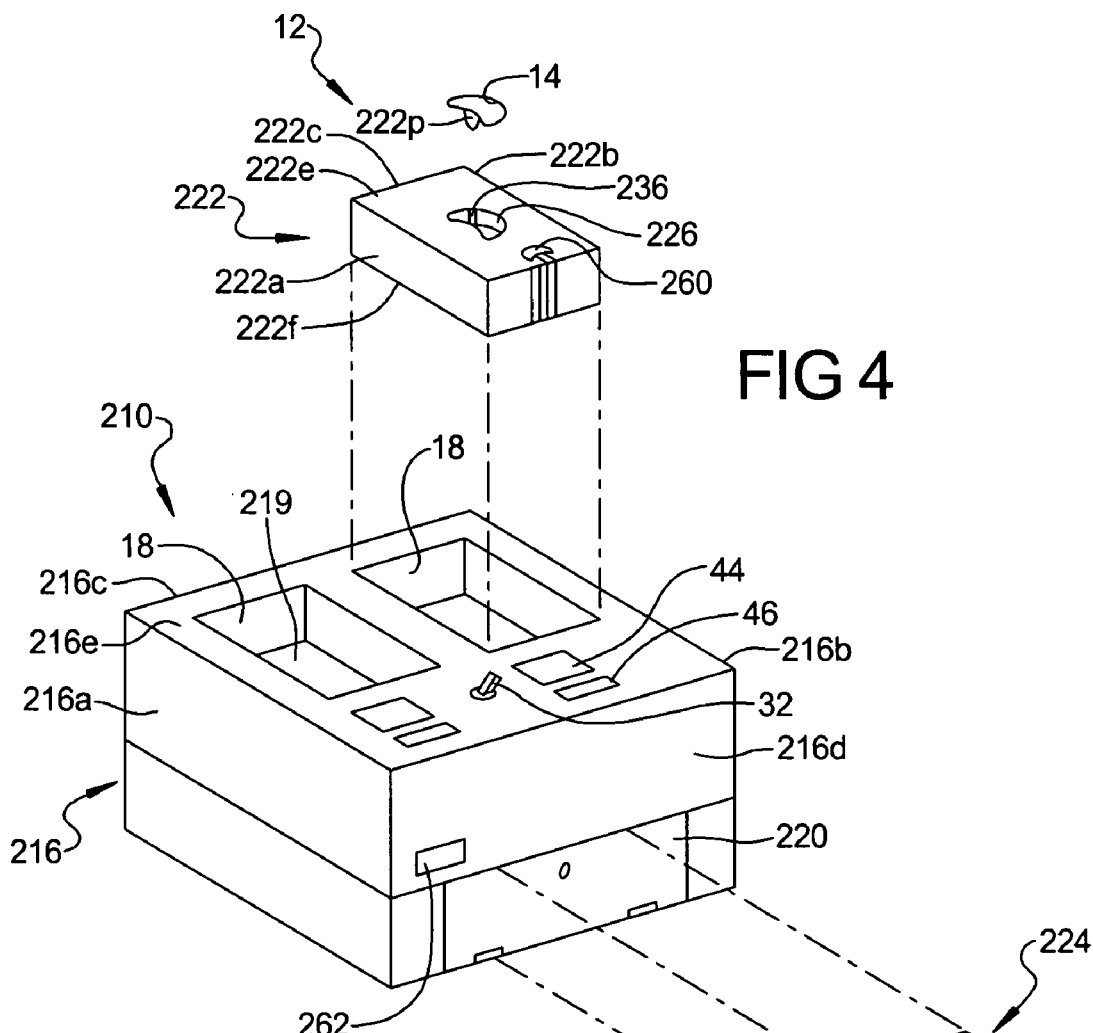
FIGS. 4-5 are perspective and side elevation section views of an alternate embodiment of a hearing aid cleaning and battery recharging device according to this invention.
Figure 5:
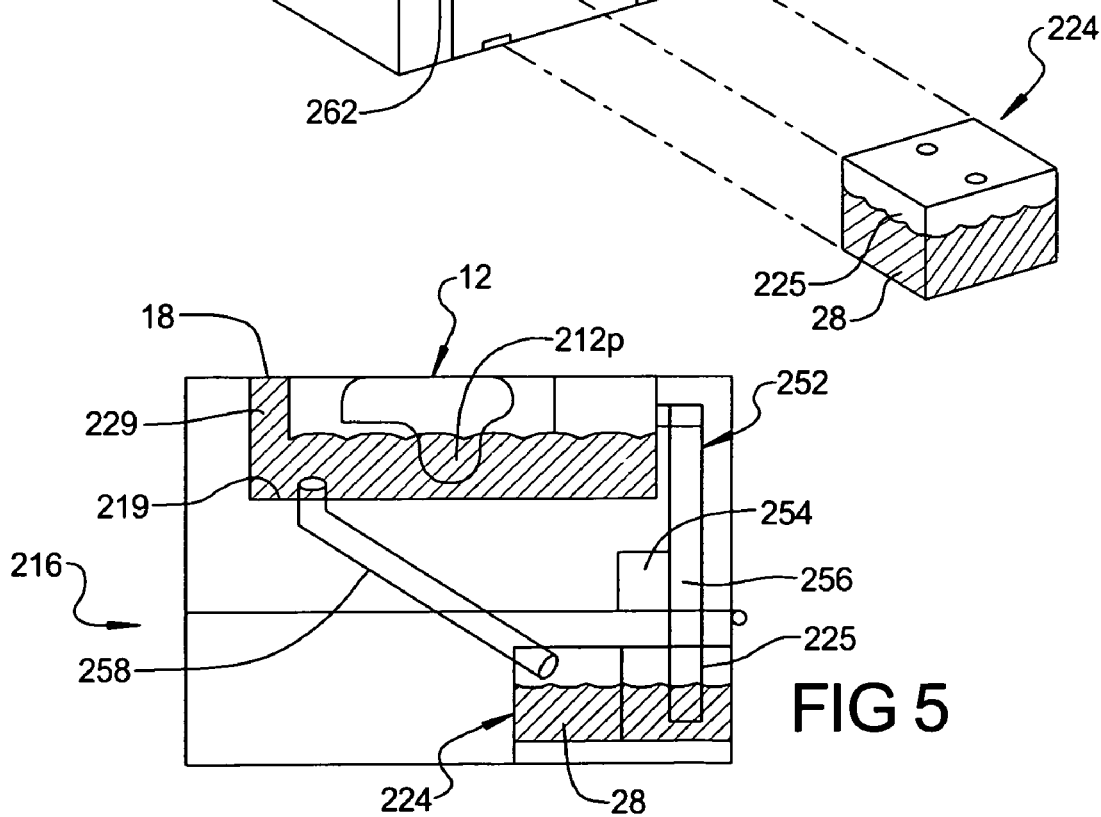

Turning now to FIGS. 4 and 5, a third embodiment of an apparatus for simultaneously cleaning and recharging the battery of a hearing aid is generally indicated by the reference number 210. In this embodiment, the apparatus 210 is similar to the apparatus 10 described herein above and includes a base member or station 216 that is provided with a pair of first chambers 18 disposed in side by side relation, each adapted to receive a respective receptacle 222, a second chamber 220, the electrical circuitry that is connectable to an exterior source of electricity, and indicators for indicating the status or condition of the cleaning fluid 28.

The switch 32 is movable between an off position, and into an on position, wherein the apparatus 210 will substantially simultaneously both clean and recharge the battery of the hearing aid.

The first chambers 18 are generally rectangular in shape and extend downwardly from the top surface 216e and into the body of the base member 216. Each chamber 18 includes an interior base wall 219 and is adapted to removably receive a receptacle 222 associated therewith.

Each receptacle 222 is generally rectangular and includes outer walls 222a-222d, a top surface 222e, and a bottom surface 222f, the outer walls and shape conforming to the rectangular shape of the chamber 18 wherein to enable the receptacle to be snugly fitted within the chamber. A through bore 226 provided with an electrical contact area 236, adapted to removably stow and make electrical contact with the contact area 14 of a hearing aid 12, extends between the surfaces 222e and 222f.

A hearing plug portion 212p of the hearing aid 12 is positioned in the receptacle 222 in a manner to extend downwardly from the bottom surface 222f and towards the base wall 219 of the chamber 18. When the hearing aid 12 is fitted into the bore 226, the electrical contact areas 14 and 236 of the hearing aid 12 and receptacle 222, respectively, are in electrical circuit relation with one another and with the electrical source, in a manner described herein above.

As described above, the outer periphery of the receptacle 222 includes an electrical contact area 38, in electrical circuit relation with the contact portion 14 of the hearing aid 12 and electrical contact area 236 in the bore 226, when the hearing aid is disposed in the bore. Additionally, a UV light 260 is provided for sterilization.

The second chamber 220 extends inwardly from a side wall 216a, is generally rectangularly shaped, and is adapted to removably receive a cleaning fluid cartridge 224 associated therewith.

The cartridge 224 is generally rectangular and includes a reservoir 225 for storing a supply of cleaning fluid 28.

Importantly, and according to this embodiment, a fluid pump system 252 is mounted in the base station 216 and hydraulically cycles the fluid 28 between the chamber 18 and the cartridge 224. In this regard, the space between the bottom surface 222f and the bottom wall 219 of the chamber 18 defines a fluid reservoir 229 that receives fluid 28, into which the hearing plug portion 212p of the hearing aid 12 is immersed.

The pump system 252 includes a pump 254, a supply tube 256, and a return tube 258. The pump 254 is fixedly mounted interiorly of the base 216 and operably connected to the supply tube 256. The supply tube 256 fluidly communicates fluid 28 between the reservoir 225 of the cartridge 224 and into the reservoir 229 of the chamber 18. The return tube 258 fluidly communicates fluid 28 from the reservoir 229 back to the reservoir 225 of the cartridge 224.

The pump 254 is in electrical circuit relation with the circuitry of the apparatus and, upon actuation of the switch 32, causes cleaning fluid 28 to be delivered to the reservoir 229 to clean the hearing aid ear plug portion 212p. Substantially simultaneously, the hearing aid battery is charged. The cleaning solution 28 pumped into the reservoir 229 of the chamber 18 will stay in there for a few hours of the cleaning process.

This solution 28 will drain back into the reservoir 225 of the fluid cartridge 224, prior to the charging cycle reaching completion, so that the hearing aid(s) can dry and be ready for use.

The apparatus 216 also includes, as discussed above, hearing aid battery charge meter 44 and light 46. Additionally, a fluid change indicator 262 is provided to indicate when the fluid 28 needs changing.

The hearing aid 12 shown above is illustrated as being kidney or peanut shaped. There are many types of hearing aids, which vary in size, power and circuitry. The different sizes and models are oftentimes characterized as in the ear aids (ITE), in the canal aids (ITC), mostly in the canal aids (MIC), completely in the canal aids (CIC), and behind the ear aids (BTE), which aids have a small case that fits behind the ear and conducts sound to the ear through an earmold that is custom made, to mention a few. Importantly, the invention herein is applicable to each of these hearing aid devices.

In general, the "in the canal" devices fit in the ear canal in varying degrees, and have greater or lesser visibility depending on how deeply the device fits within the ear. The completely in the canal instrument fits down deep into the ear canal and is the least visible of the hearing aids styles. At the other end is the custom made instrument that fits entirely within the ear canal, and the most visible of the in the canal models.

Additionally, in view of the expanding use of cell-phones, laptop computers, WI-FI, and other data transmitting apparatus, the invention herein is applicable for use with wireless hearing aid devices, such as those incorporating Bluetooth and other RF transmitting protocols. Bluetooth is emerging as a positive improvement for those who wear hearing instruments and use cell-phone headsets in combination with their hearing aids.

Generally, the Bluetooth enabled hearing aid is of the behind the ear type and allows communication with a mobile phone. The hearing aid is housed in a small case fitting over the ear. The hearing aid is held in place by a custom earmold. A thin clear tube goes from the hearing aid behind the ear into the ear canal. The signal transmitted between the hearing aid and phone devices is digital, and not subject to the same sources of interference as other types of wireless transmission, such as analog FM or analog inductive transmission.

The invention is not limited for use just with hearing aids but is also applicable to Bluetooth enabled headsets and/or earbuds.

Having described preferred embodiments of my invention it is obvious that the invention described above is susceptible to many variations, modifications and changes without departing from the spirit of the invention or the scope of the appended claims. It should be understood that the invention is not to be limited except as by the appended claims.

I claim:

1. An apparatus for cleaning and recharging at least one hearing aid of the type having an electrical contact on the outer periphery thereof and a rechargeable battery in the interior, comprising:
    a base member, said base member including first and second chambers,
    a receptacle having a cavity for stowing the hearing aid, said receptacle removably mountable in said first chamber and said cavity having a cavity wall in gripping fitment, at least in part, with the outer periphery and the electrical contact of said hearing aid,
    a reservoir for storing a supply of cleaning fluid, said reservoir provided in said second chamber,
    electrical circuitry for connecting the electrical contact of said hearing aid, said receptacle, said cavity wall, and the reservoir for storing fluid in electrical circuit relation;
    means for connecting the electrical circuitry with a source of electricity;
    a switch to selectively place the apparatus in a selected mode, including an off mode, a cleaning only mode, and a battery recharge only mode,
    indicators in the form of meters to indicate the condition of the cleaning fluid, and
    actuatable lights to provide visual output indicating the condition of the cleaning fluid.

2. The apparatus according to claim 1, wherein the condition comprises viability and pH of the cleaning fluid, the battery charge level, and the time and number of times the apparatus was operated.

3. An apparatus for simultaneously cleaning the ear plug and recharging the battery of a hearing aid, the hearing aid including an electrical contact on the outer periphery thereof and a rechargeable battery in the interior in electrical circuit relation with the contact, comprising:
    a base station including a top surface and a side wall, a first chamber extending from the top surface into the base and terminating in an interior base wall, and a second chamber extending from the side wall into the into the base,
    a receptacle for mounting the hearing aid, the receptacle removably mounted in the first chamber and having an outer periphery, top and bottom surfaces, and a bore for mounting the hearing aid, aid bore extending between the surfaces and having a wall, at least in part, for engaging the outer periphery of the hearing aid,
    said first chamber having an interior wall, at least in part, for engaging the outer periphery of said receptacle and positioning the bottom surface in spaced relation from the bottom wall of said second chamber to form a first reservoir, and said hearing aid ear plug being proximate to the bottom wall when the receptacle is mounted in the first chamber,
    a fluid cartridge removably mounted in said second chamber, said cartridge forming a second reservoir,
    a pump, said pump including means for communicating fluid from said second reservoir to said first reservoir,
    means for communicating fluid from said first reservoir to said second reservoir,
    electrical circuitry for connecting the electrical contact of said hearing aid, said receptacle, the wall of said bore, the reservoir for storing fluid, and the pump in electrical circuit relation with one another; and
    means for connecting the electrical circuitry with a source of electricity.

4. The apparatus according to claim 3, further comprising a switch to selectively place the apparatus in a selected mode, including an off mode, and an actuated mode, wherein the apparatus simultaneously cleans the ear plug and recharges the battery of the hearing aid.

5. The apparatus according to claim 4, further comprising indicators in the form of meters provided with actuatable lights to provide visual output indicating the condition of the cleaning fluid, said conditions including viability and pH of the cleaning fluid, the battery charge level, and the time and number of times the apparatus was operated.

6. The apparatus according to claim 5, wherein at least two hearing aids may be cleaned and/or have their batteries recharged.

* * * * *